United States Patent
Bassin

(10) Patent No.: US 10,449,312 B2
(45) Date of Patent: *Oct. 22, 2019

(54) METHODS AND APPARATUS FOR THE SYSTEMIC CONTROL OF VENTILATORY SUPPORT IN THE PRESENCE OF RESPIRATORY INSUFFICIENCY

(71) Applicant: ResMed Limited, Bella Vista (AU)

(72) Inventor: David John Bassin, Coogee (AU)

(73) Assignee: ResMed Pty Ltd (AU)

( * ) Notice: Subject to any disclaimer, the term of this patent is extended or adjusted under 35 U.S.C. 154(b) by 948 days.

This patent is subject to a terminal disclaimer.

(21) Appl. No.: 14/490,933

(22) Filed: Sep. 19, 2014

(65) Prior Publication Data

US 2015/0000667 A1    Jan. 1, 2015

Related U.S. Application Data

(63) Continuation of application No. 10/596,034, filed as application No. PCT/AU2004/001651 on Nov. 25, 2004, now Pat. No. 8,869,795.

(Continued)

(51) Int. Cl.
*A61M 16/00* (2006.01)
*A61M 16/06* (2006.01)
(Continued)

(52) U.S. Cl.
CPC ........ *A61M 16/0069* (2014.02); *A61M 16/00* (2013.01); *A61M 16/0003* (2014.02);
(Continued)

(58) Field of Classification Search
CPC .......................... A61M 16/00; A61M 16/0069
See application file for complete search history.

(56) References Cited

U.S. PATENT DOCUMENTS

| | | |
|---|---|---|
| 4,944,310 A | 7/1990 | Sullivan |
| 4,986,268 A | 1/1991 | Tehrani |

(Continued)

FOREIGN PATENT DOCUMENTS

| | | |
|---|---|---|
| DE | 19516536 A1 | 11/1996 |
| EP | 1086716 A2 | 3/2001 |

(Continued)

OTHER PUBLICATIONS

Australian Examination Report for Application No. 2010206082 dated Jun. 8, 2012.

(Continued)

*Primary Examiner* — LaToya M Louis
(74) *Attorney, Agent, or Firm* — Botos Churchill IP Law LLP

(57) ABSTRACT

A method and apparatus for providing ventilatory assistance to a spontaneously breathing patient. An error signal is computed that is the difference between a function of respiratory airflow over a period of time and a target value. Using a servo loop, air is delivered to the patient at a pressure that is a function of the error signal, the phase of the current breathing cycle, and a loop gain that varies depending on the magnitude of the error signal. The loop gain increases with the magnitude of the error signal, and the gain is greater for error signals below a ventilation target than for error signals above the ventilation target value. The target value is an alveolar ventilation that takes into account the patient's physiologic dead space.

37 Claims, 7 Drawing Sheets

Related U.S. Application Data

(60) Provisional application No. 60/525,219, filed on Nov. 26, 2003.

(51) Int. Cl.
*A61M 16/08* (2006.01)
*A61B 5/087* (2006.01)

(52) U.S. Cl.
CPC ........ *A61M 16/0051* (2013.01); *A61M 16/06* (2013.01); *A61M 16/0875* (2013.01); *A61B 5/087* (2013.01); *A61M 2016/0033* (2013.01); *A61M 2016/0039* (2013.01); *A61M 2205/15* (2013.01); *A61M 2205/50* (2013.01); *A61M 2230/005* (2013.01); *A61M 2230/40* (2013.01)

(56) References Cited

U.S. PATENT DOCUMENTS

| | | |
|---|---|---|
| 5,319,540 A | 6/1994 | Isaza et al. |
| 5,535,738 A | 7/1996 | Estes et al. |
| 5,645,054 A | 7/1997 | Cotner et al. |
| 5,701,883 A | 12/1997 | Hete et al. |
| 6,321,748 B1 | 11/2001 | O'Mahoney |
| 6,363,933 B1 | 4/2002 | Berthon-Jones |
| 6,532,957 B2 | 3/2003 | Berthon-Jones |
| 6,532,959 B1 | 3/2003 | Berthon-Jones |
| 6,532,960 B1 | 3/2003 | Yurko |
| 6,622,726 B1 | 9/2003 | Du |
| 6,644,312 B2 | 11/2003 | Berthon-Jones et al. |
| 6,739,336 B1 | 5/2004 | Jalde et al. |
| 6,773,404 B2 | 8/2004 | Poezevera et al. |
| 6,910,480 B1 | 6/2005 | Berthon-Jones |
| 2001/0027792 A1* | 10/2001 | Berthon-Jones ...... A61M 16/00 128/204.23 |
| 2001/0035186 A1 | 11/2001 | Hill |
| 2002/0088465 A1 | 7/2002 | Hill |
| 2003/0121519 A1 | 7/2003 | Estes et al. |

FOREIGN PATENT DOCUMENTS

| | | |
|---|---|---|
| EP | 1129742 A2 | 9/2001 |
| EP | 1346743 A1 | 9/2003 |
| FR | 2698274 A1 | 5/1994 |
| JP | 5150802 A | 6/1993 |
| JP | 06000525 A | 1/1994 |
| JP | 2000516491 A | 12/2000 |
| JP | 2001500416 A | 1/2001 |
| JP | 2001037880 A | 2/2001 |
| JP | 2001046503 A | 2/2001 |
| JP | 2001286564 A | 10/2001 |
| JP | 2001293088 A | 10/2001 |
| JP | 2002315831 A | 10/2002 |
| WO | 92/11054 A1 | 7/1992 |
| WO | 9308857 A1 | 5/1993 |
| WO | 9806449 A1 | 2/1998 |
| WO | 1998012965 A1 | 4/1998 |
| WO | 99/61088 A1 | 12/1999 |
| WO | 200078379 A1 | 12/2000 |
| WO | 0119440 A1 | 3/2001 |

OTHER PUBLICATIONS

European Examination report for Application No. 10162336.1 dated Mar. 14, 2011.
Extended European Search Report for Application No. 10162336 dated Jun. 17, 2010.
International Search Report and Written Opinion for Application No. PCT/AU2004/01651 dated Jan. 17, 2005.
Japanese Office Action for Application No. P2011-000259 dated Aug. 7, 2012.
Laubscher T, et al. An adaptive lung ventilation controller. IEEE transactions on biomedical engineering 1994, 41 :51-59.
West, John B., "Respiratory Physiology", The Essentials 5th Edition, 1995, pp. 17-19.
European Search report for Application No. EP 11 17 7682.9 dated Dec. 13, 2017, 3 pages.

* cited by examiner

METHODS AND APPARATUS FOR THE SYSTEMIC CONTROL OF VENTILATORY SUPPORT IN THE PRESENCE OF RESPIRATORY INSUFFICIENCY

CROSS-REFERENCE TO RELATED APPLICATIONS

The present application is a continuation of U.S. patent application Ser. No. 10/596,034, filed on Jan. 31, 2007, which application is a national phase entry under 35 U.S.C. § 371 of International Application No. PCT/AU04/01651 filed Nov. 25, 2004, which claims priority from U.S. Provisional Patent Application No. 60/525,219 filed Nov. 26, 2003, all of which are hereby incorporated herein by reference.

FIELD OF THE INVENTION

This invention relates to methods and apparatus for the provision of ventilatory assistance synchronized with a patient's respiratory cycle and controlled to provide a minimum sufficient level of support in the presence of respiratory insufficiency.

BACKGROUND OF THE INVENTION

Respiratory insufficiency is an abnormality of the respiratory system with an adverse effect on gas exchange, resulting in a lowering of the arterial partial pressure of oxygen, an increase in the arterial partial pressure of carbon dioxide, or both. It may be due to a decrease in ventilation in the presence of normal lungs, a lung abnormality, or a combination of these.

Respiratory insufficiency generally results in worse gas exchange during sleep, for a variety of reasons including decreased respiratory drive and postural factors. The decrease in voluntary muscle function during REM sleep may cause a marked worsening of respiratory function during this stage of sleep, depending on the importance of the accessory muscles of respiration in the particular patient.

Sleep may be associated with varying degrees of upper airway obstruction, referred to as obstructive sleep apnoea (OSA).

Sleep-disordered breathing (SDB) generally refers to types of breathing disruption that occur during sleep. The most common form of sleep-disordered breathing is obstructive sleep apnea (OSA). Loud, intermittent snoring, apneas, and hypopneas characterize OSA.

Respiratory insufficiency, and possibly OSA, occur in conjunction with conditions experienced by patients with chest wall, neuromuscular, amyotrophic lateral sclerosis (ALS), or lung disease, such as chronic obstructive pulmonary disease (COPD). Because the symptoms of sleep apnea present themselves as a result of a precursor, SDB has become the general term used to describe any disease state that manifests apneas and/or hypopneas during sleep. Apneas and hypopneas interfere with gas exchange, fragment sleep, and frequently cause oxygen desaturations. In severe cases, patents may experience these oxygen desaturations and arousals from sleep hundreds of times each night.

The most common treatment of OSA is to administer continuous positive airway pressure (CPAP). CPAP was invented by Sullivan and taught in U.S. Pat. No. 4,944,310. Briefly stated, CPAP treatment acts as a pneumatic splint of the airway by the provision of a positive pressure, usually in the range 4-20 cm $H_2O$. The air is supplied to the airway by a motor driven blower whose outlet is coupled by an air delivery hose to a nose (or nose and/or mouth) mask sealed with the patient's face. An exhaust port is provided in the delivery tube proximate to the mask.

Ventilatory assistance may be provided by bi-level ventilators, proportional assist ventilators and servo-controlled ventilators. Each type of ventilator utilizes different methods for assisting with patient respiration and achieves different goals.

Such ventilator devices provide appropriate responses to the changing conditions of the patient. For example, ventilatory devices determine when to trigger and cycle varying pressure levels associated with inspiratory and expiratory support so that the device will synchronize with the respiratory cycle of the patient. Triggering is the event associated with the initiation of the pressure levels intended for the patient's inspiration. Cycling is the event associated with switching to the pressure levels intended for the patient's expiration. Also, the devices may provide some method for increasing or decreasing ventilation during periods of hypoventilation or hyperventilation respectively. Maximizing machine performance in either or both of these areas generally results in greater patient comfort and better treatment of respiratory insufficiency.

Simple bi-level ventilators provide a higher pressure during the inspiratory portion of the patient's breathing cycle, a so-called IPAP, and a lower pressure during the expiratory portion of the breathing cycle, a so-called EPAP. Traditionally, the switching may be accomplished by monitoring the respiratory flow or pressure and defining a threshold level. When the measured value exceeds the threshold, the device will trigger the IPAP pressure. When the measured value falls below the threshold, the device will cycle to the EPAP pressure. Other alternatives to such switching involve recorded respiration rates and the monitoring of elapsed time from the start of either inspiration or expiration. The machine may switch to the following portion of the respiratory cycle, either inspiration or expiration, after reaching the expected time for the previous part of the respiratory cycle.

A different servo-ventilator device developed by ResMed Ltd. accomplishes synchronization by delivering smooth cyclical pressure changes based on a calculated instantaneous phase. Embodiments of the apparatus are the subjects of commonly owned U.S. patent application Ser. No. 09/661,998 and U.S. Pat. Nos. 6,532,957 and 6,532,959, the disclosures of which are incorporated herein by reference. Generally, the apparatus provides an instantaneous mask pressure P(t) based upon a fraction of the patient's airway resistance R (this fraction ranging from zero to a substantial value but less than 1), respiratory airflow f(t), an amplitude A, and an estimation of the patient's instantaneous respiratory phase $\phi$ as applied to a pressure waveform template $\pi(\phi)$ as follows:

$$P(t)=P_G+Rf(t)+A\pi(\phi) \text{ for all } f(t) \quad \text{(inspiration and expiration)}$$

where:

$$A=G\int(V(t)-V_{TGT})dt$$

$$A_{MIN} < A < A_{MAX}, \text{ and}$$

$P_o$ is an initial pressure.

In this type of ventilator, V(t) can be, for example, one half the absolute value of the respiratory airflow f(t). The ventilation target $V_{TGT}$ may be a percentage of a measured volume of airflow, e.g., 95% of the average minute volume or a preset prescribed minute volume. G is the gain of the integral servo-controller, values in the range 0.1-0.3 cmH$_2$O per L/min error in ventilation per second being suitable. $A_{MIN}$ and $A_{MAX}$ are limits set on the degree of support A for comfort and safety. The limits 0.0 and 20.0 cmH$_2$O respectively are generally suitable.

In detecting the patent's respiratory phase, the apparatus uses a respiratory airflow signal and its derivative as input data for a set of fuzzy logic rules that are associated with particular phases of respiration. Using the results of the evaluations of the rules, a single continuous phase variable is derived and used as the instantaneous respiratory phase. This phase value as applied to a pressure waveform template then proportionally varies the delivered pressure in a manner that generates a realistic and comfortable respiratory cycle. Simultaneously, the calculation of A based on the target ventilation $V_{TGT}$ guarantees a desired level of ventilation.

With regard to the issue of synchronization, while determining continuous instantaneous phase has its benefits in detecting the patient's respiratory cycle, it may be desirable to use a method for determining the pressure to be delivered to a patient which does not use a simple function $\pi(\phi)$ to determine the number by which A in the above equation is multiplied. It may also be beneficial to utilize alternative methods for triggering the initiation of inspiratory pressure.

With regard to the control of a pressure response to changing patient respiratory needs, in the above equation the rate of change of pressure support is simply proportional to the difference between the target ventilation and the actual ventilation. It may be desirable for small errors to result in a gentler response, and in particular for marked hypoventilation to result in a more brisk response, since it is much more likely to result in significant hypoxia. By contrast, when measured ventilation is well above target, it may not be necessary or desirable to briskly decrease the ventilatory support level, particularly considering that when there has been a sudden change in leak in a noninvasive ventilatory system, the measured ventilation is almost always greater than the actual ventilation until the leak estimation system has substantially compensated for the change in leak.

A problem with ventilators that target total ventilation (traditionally called "minute ventilation") is that total ventilation may not provide an accurate measure of the extent to which the actual needs of the patient are met. Such a measure does not account for the fact that patients have anatomical and physiological deadspace, and that the deadspace varies between patients. In particular, with a particular total ventilation, a high respiratory rate and a low tidal volume will provide lower alveolar ventilation than a low respiratory rate and a high tidal volume. A device which servocontrols minute ventilation is thus at risk of providing inadequate alveolar ventilation at high respiratory rates.

BRIEF SUMMARY OF THE INVENTION

It is an objective of the invention to provide a ventilator synchronized with a patient's respiratory cycle to provide a higher level of pressure support during inspiration and a lower level of pressure support during expiration.

It is a further objective of the invention to provide such a synchronized ventilator that is flow triggered but phase cycled.

It is a still further objective of the invention to provide a ventilator that maintains at least a target ventilation and responds to the error in ventilation in a way which is not linear with respect to the error and not symmetrical about zero error.

It is another objective of the invention to provide a ventilator which uses two measures of ventilation which respond at different speeds to allow both smooth variation in pressure support and gain being a function of error, while still providing rapid response to marked hypoventilation.

It is another objective of the invention to provide a ventilator which servocontrols alveolar ventilation.

Additional objectives will be apparent to those skilled in the art upon consideration of the following description of the invention.

One aspect of the invention involves patient-ventilator synchronization. In accordance with the invention, flow is measured. With the measure of flow, an instantaneous breath phase variable is determined using a fuzzy logic method. The ventilator then will trigger an inspiratory pressure for ventilatory support intended for the patient's inspiration when the measured flow exceeds a threshold. The ventilator subsequently cycles to deliver an expiratory pressure when the instantaneous phase passes a certain threshold value, such as 50%.

Another aspect of the invention relates to the delivery of servo-controlled ventilatory support to maintain a target ventilation. Adjustment of the delivered ventilatory support is based on the error between a target and actual measure, and a gain which varies with the distance of the actual measure from the target. Alternatively, it may be a function of relative ventilation error (which is defined to be ventilation error divided by target ventilation). This varying gain permits subdued ventilatory support responses for mild changes in patient ventilation while permitting more vigorous responses to more severe changes. In a simple form, a step function provides a lower gain if the distance from the target is less than a threshold and higher gain otherwise. The gain may be altered symmetrically around the target or alternatively asymmetrically. In an asymmetrical embodiment, the gain may change differently depending on whether the patient's ventilation is above or below the desired or target ventilation. These tempered or graduated gain adjustments permit the device to make a relatively greater increase (i.e., a more aggressive response) in pressure support when measured ventilation is further from the target, i.e., there is a large target error, than when measured ventilation is closer to the target, i.e., there is a small target error. It also permits making less aggressive changes to the gain for hyperventilation and more aggressive changes for hypoventilation.

In another aspect of the invention, control of ventilation is more accurately achieved by controlling a measure of alveolar ventilation. Since the airways contain dead space, only a portion of the air inhaled by a patent can participate in gas exchange. In accordance with the invention, the total ventilation is corrected by subtracting the effect of anatomical and/or physiological dead space as an estimate of a target alveolar ventilation. This alveolar ventilation is utilized as a target and compared with a similarly calculated actual measure made during the delivery of ventilatory support. The target error of these two terms is then applied to adjust the pressure support provided by the ventilator.

According to the invention, an error signal is computed that is the difference between a function of respiratory airflow over a period of time and a target value. Using a servo loop, breathing gas is delivered to the patient at a pressure that is a function of the error signal, the phase of the current breathing cycle, and a loop gain that varies depending on the magnitude of the error signal. The loop gain increases with the magnitude of the error signal, and the gain is greater for error signals below a ventilation target value than for error signals above the ventilation target value. The target value is an alveolar ventilation that takes into account the pabent's physiologic dead space.

DETAILED DESCRIPTION

Figure 1:
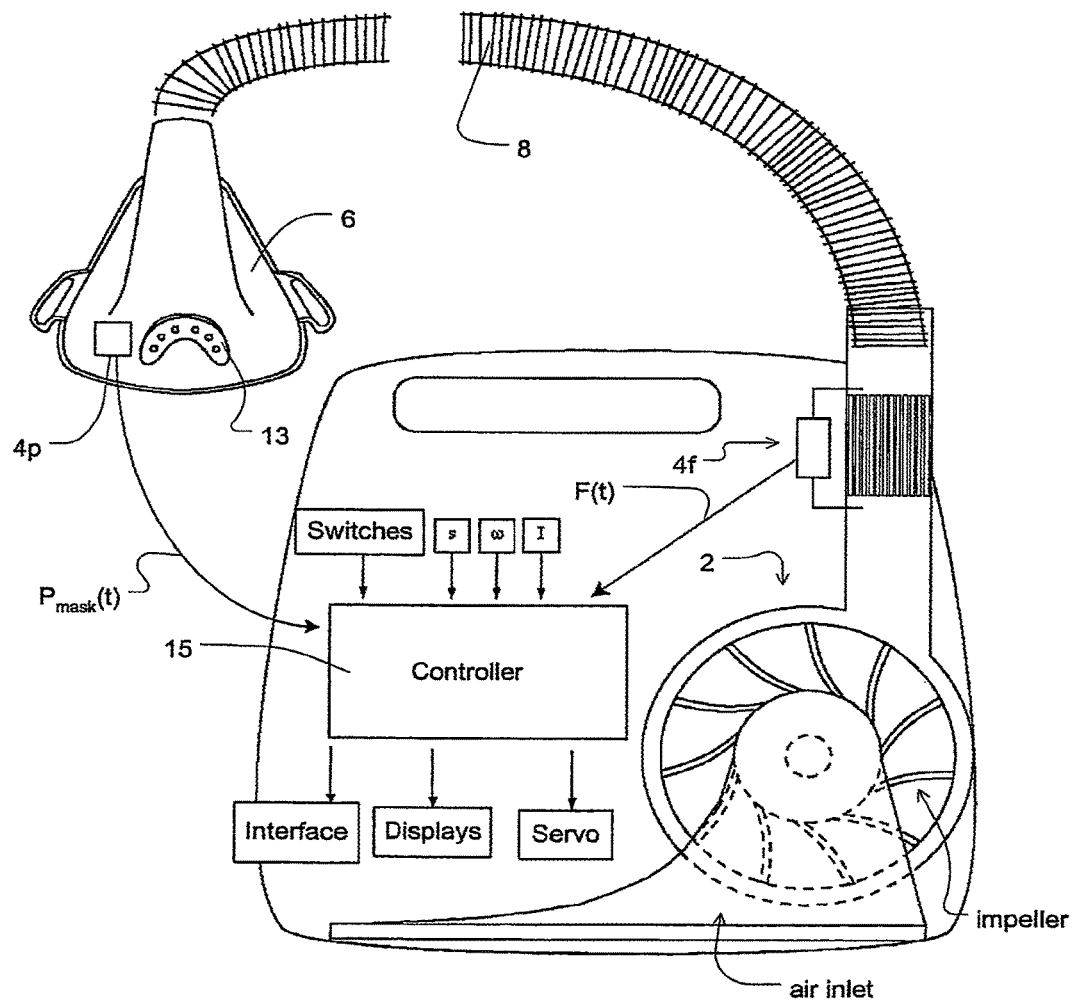
FIG. 1 depicts the structure of the preferred ventilator apparatus for implementing the methods of the current invention.

In reference to FIG. 1, the ventilator relies on a servo-controlled loop for governing the operation of blower 2. The device includes a flow sensor 4f, pressure sensor 4p, a mask 6, and an air delivery conduit 8 for connection between the blower 2 and the mask 6. Exhaust gas is vented via exhaust 13. Mask flow may be measured using a pneumotachograph and differential pressure transducer to derive a flow signal F(t). Alternatively, the pneumotachograph may be replaced by a bundle of small tubes aligned in parallel with the flow from the blower with the pressure difference measured by the differential pressure transducer across the bundle. Mask pressure is preferably measured at a pressure tap using a pressure transducer to derive a pressure signal $P_{mask}(t)$. The pressure sensor 4f and flow sensor 4p have been shown only symbolically in FIG. 1 since those skilled in the art will understand how to measure flow and pressure. Flow F(t) and pressure $P_{mask}(t)$ signals are sent to a controller or microprocessor 15 to derive a pressure request signal $P_{Request}(t)$. The controller or processor includes integrated chips, a memory and/or other instruction or data storage medium to implement the control methodology described in more detail herein. Programmed instructions with the control methodology are either coded on integrated chips in the memory of the device or loaded as software.

A. Pressure Delivery Synchronization—Triggering and Cycling

One aspect of the invention involves patient ventilator synchronization. In the preferred device, synchronization is performed by a unique combination of two different respiratory cycle detection techniques that collectively result in superior synchronization. It has been found that a ventilator controlled by application of flow-based triggering in conjunction with phase-based cycling as described herein has a synergistic effect in terms of improved machine synchronization.

In general, the ventilator delivers a higher pressure upon the detection of patient inspiration and a lower pressure during expiration. One simple form of the delivered pressure as cycled by the controller is as follows:

$P(t)=P_o+A$           if inspiration is true $P(t)=0$           if inspiration is not true (i.e. expiration)

where:

$A=-G\int(V(t)-V_{TGT})dt$ $0 \leq A_{min} \leq A \leq A_{max}$ (chosen for safety and comfort)

$P_o$ is an initial pressure, and $G$ is a gain.

While the above pressure formula will generally result in a higher pressure and a lower pressure during the inspiratory and expiratory portions of a respiratory cycle of a patient in a bi-level sense, those skilled in the art will recognize that the pressure changes may be ramped to provide more comfortable transitions from the higher to lower pressure or lower to higher pressure such that the ramping simulates a more natural respiratory airflow cycle.

Figure 2:
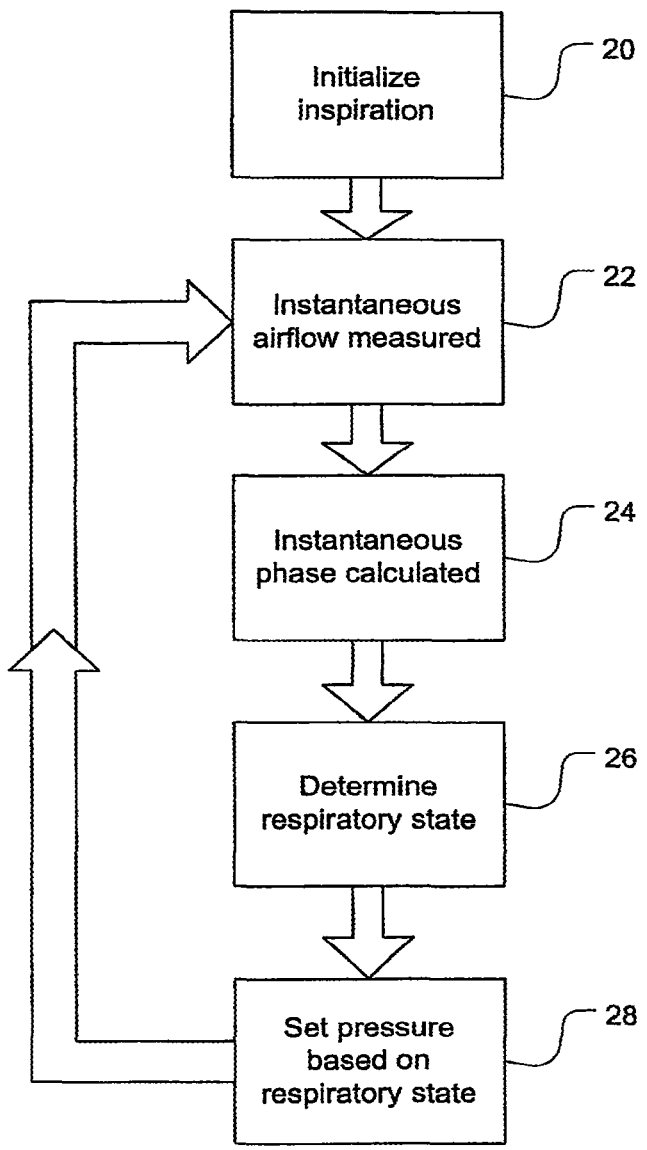
FIG. 2 is a flow chart of the general steps in synchronizing and setting the pressure.

The steps in the methodology for triggering to the higher pressure and cycling to the lower pressure are listed in the flow chart of FIG. 2. In step 20, the current state of the machine is initialized to inspiration. In step 22, an instantaneous airflow is measured. In step 24, the patient's instantaneous phase is calculated. In step 26, the setting of the machine's state (inspiration or not inspiration) is based upon an evaluation of the airflow and instantaneous phase to determine the respiratory state of the patient. In step 28, the pressure is adjusted based upon the detected respiratory state. The steps repeat at a very high frequency relative to a normal respiratory cycle with the exception of the initialization step 20.

With regard to steps 24 and 26, those skilled in the art will recognize an appropriate threshold and instantaneous flow measure suitable for detecting the onset of inspiration, which will also be adjusted to alleviate the effect of leak. As it relates to the calculation of instantaneous phase, the invention contemplates a continuous phase variable as disclosed in U.S. patent application Ser. No. 09/661,998 or U.S. Pat. No. 6,532,957. The instantaneous phase variable is calculated in a fuzzy logic process.

More specifically, the device utilizes a respiratory airflow and preferably its rate of change. The degree of membership of the respiratory airflow signal in each of the fuzzy sets zero, positive, large positive, negative, and large negative is calculated using suitable membership functions. Similarly, the degree of membership of the derivative of the respiratory airflow signal in each of the fuzzy sets steady, increasing, increasing fast, decreasing and decreasing fast is calculated using suitable membership functions. The degrees of membership in these sets are used in a group of fuzzy logic inference rules. Each fuzzy inference rule is associated with a particular phase of respiration. Although many variations are possible, in the preferred embodiment the inference rules relating to respiratory airflow are as follows:

1. If the airflow is zero and increasing fast, then the phase is 0 revolutions.

2. If the airflow is large positive and steady, then the phase is 0.25 revolutions.

3. If the airflow is zero and falling fast, then the phase is 0.5 revolutions.

4. If the airflow is large negative and steady, then the phase is 0.75 revolutions.

5. If the airflow is zero and steady and the 5-second low-pass filtered absolute value of the respiratory airflow is large, then the phase is 0.9 revolutions.

6. If the airflow is positive and the phase is expiratory, then the phase is 0.1 revolutions.

7. If the airflow is negative and the phase is inspiratory, then the phase is 0.6 revolutions.

8. If the 5-second low-pass filtered absolute value of the respiratory airflow is small, then the phase in the respiratory cycle is increasing at a fixed rate equal to the patient's expected respiratory rate.

9. If the 5-second low-pass filtered absolute value of the respiratory airflow is large, then the phase in the respiratory cycle is increasing at a steady rate equal to the existing rate of change of phase, low-pass filtered with a time constant of 20 seconds.

The general method for developing and using these fuzzy inference rules is described in U.S. patent application Ser. No. 08/935,785 or U.S. Pat. No. 6,532,957. Generally, various features, such as the point of start of inspiration, are identified on a graph of airflow versus phase, and for each phase corresponding fuzzy rules are developed. For example, a suitable rule for the point "start of inspiration" could be "effort signal is small and the second derivative of the effort signal with respect to time is large positive." Membership functions, would cause that rule to be maximally activated at or near the start of inspiration. Preferably, the exact phase at the moment of maximal activation should be determined empirically. In the current example, the maximum activation will be at a phase shortly after the actual moment of start of inspiration, say 0.05 revolutions, and this is the best phase to associate with the rule. The more features that are identified and assigned a rule and a phase, the smoother will be the resultant determination of instantaneous phase. Additional rules may be supplied so that the phase will continue to rotate at an. expected respiratory rate in the presence of an apnea or leak. Sample rules 8 and 9 serve these purposes respectively.

Each of the rules in the combined set of fuzzy inference rules will be evaluated to determine a degree of activation $G(n)$ by using a standard fuzzy inference method. For example, with respect to rule 2, using one such method assuming a unit weighting of rules, if (a) the degree of truth for the membership function "the airflow is large positive" evaluates to 0.6 and (b) the degree of truth for the membership function "the airflow signal is steady" evaluates to 0.4, and a fuzzy logic "AND" operator is applied, then the degree of activation for $G(2)$ would be 0.4.

Additionally, each of the fuzzy inference rules associates a particular rule with a particular phase $\Phi(n)$. For example, as shown above, rule 2 is associated with $\Phi(2)=0.25$ revolutions. Then, using the degree of activation $G(n)$ for each $\Phi(n)$, a single value representing the instantaneous respiratory phase $\Phi$ is calculated in a defuzzification step using the formula:

$$\Phi = \arctan(\Sigma[G(n)\sin \Phi(n)], \Sigma[G(n)\cos \Phi(n)]).$$

where the arctan function is a four-quadrant function, giving a phase of 0 in the unlikely event that both its arguments are zero. In the preferred embodiment, the instantaneous respiratory phase $\Phi$ is a continuous variable between 0 and 1 revolution, which proportionally represents a position within a singe respiratory cycle (starting at the beginning of inspiration (0) and ending at the conclusion of expiration (1)). Of course, those skilled in the art will recognize that the instantaneous respiratory phase can be represented by a different numerical range.

As previously described, the delivered pressure is flow-triggered and phase cycled. This change in machine state is accomplished in step 26. One algorithm for achieving the invention is as follows:

If (inspiration is true) and (instantaneous phase is greater than an instantaneous phase threshold), then:
  set Inspiration to false (i.e., expiration detected)
Otherwise, if (inspiration is false) and (instantaneous airflow is greater than a flow threshold), then:
  set Inspiration to true (i.e., inspiration detected).

Figure 3:
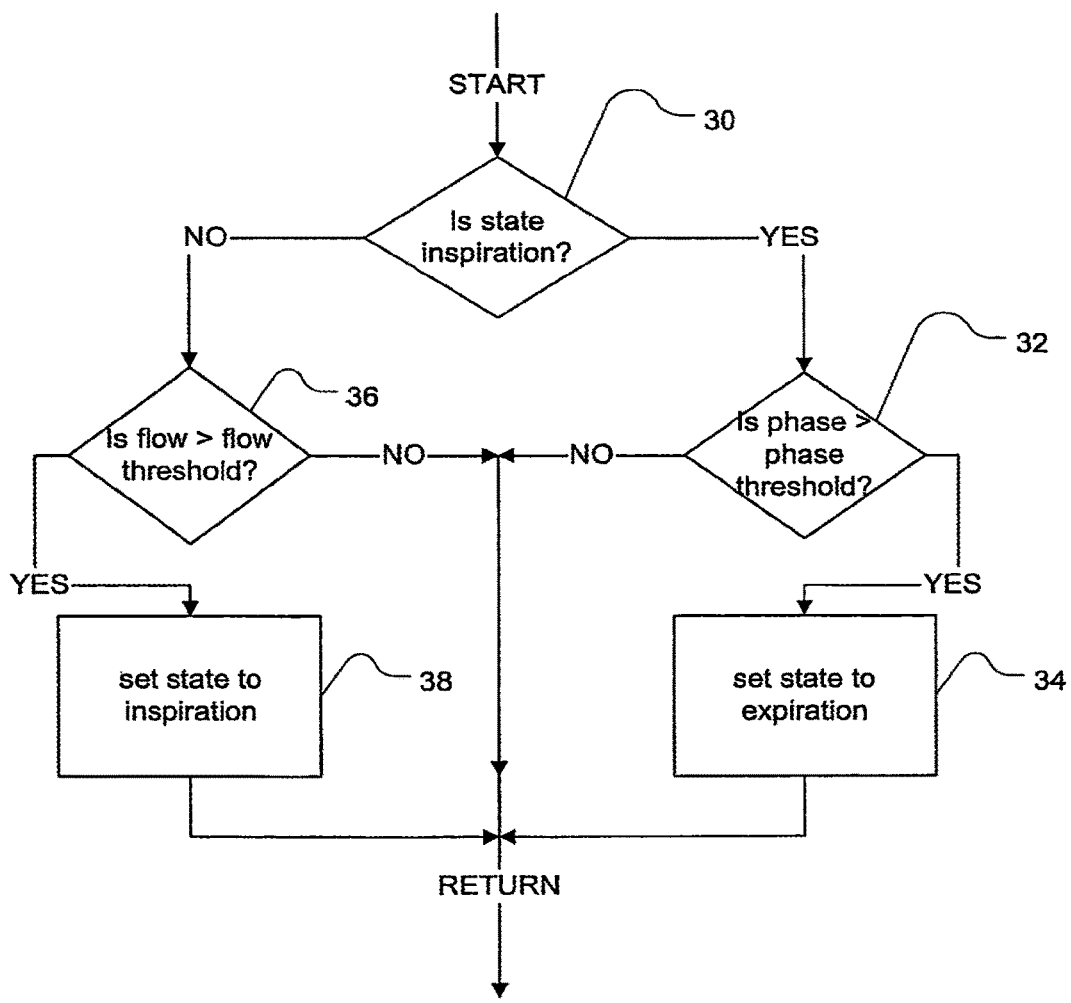
FIG. 3 is a flow chart showing steps to achieve flow triggering and phase cycled machine synchronization.

The steps in such an algorithm are illustrated in the flow chart of FIG. 3. In step 30 the apparatus examines the current respiratory state. If the current state is inspiration, the instantaneous phase is compared to a phase threshold in step 32. The phase threshold in the preferred embodiment is 0.5 revolutions but would be different depending on the numerical range of the instantaneous phase as it has been associated with one compete respiratory cycle. A central number in the range that would represent the switching point between inspiration and expiration would be appropriate. In step 32, if the instantaneous phase is greater than the threshold, step 34 is executed, otherwise no change to the machine's state will occur. In step 34, the machine's state will be set to expiration.

If the state is not inspiration in step 30, step 36 compares an instantaneous measured flow with an airflow threshold. If the flow is greater than the threshold, a change of machine state will occur in step 38, otherwise no change will occur. In step 38 the machine's state will be switched to inspiration.

With this process, when the measure of the instantaneous flow exceeds the flow threshold while the machine is delivering an expiratory level of pressure, the machine will trigger the inspiratory pressure because the apparatus has effectively detected the onset of inspiration. Moreover, when the calculated instantaneous phase exceeds the phase threshold while the machine is delivering an inspiratory level of pressure, the machine will cycle to the expiratory pressure because the apparatus will have effectively detected the onset of expiration or otherwise detected a need to cycle to the onset of expiration.

B. Controller Gain Varying with Ventilation Error

In order to insure a proper ventilation of a patient in the presence of varying respiratory effort and patient condition, the pressure delivered $P(t)$ during inspiration is set as a function of a target ventilation $V_{target}$ and actual ventilation $V_{actual}$, by adjustment of amplitude A. With a feedback measure of ventilation $V_{actual}$, the support is servo-controlled to satisfy the target ventilation $V_{target}$. The calculation of the delivered pressure support amplitude A is as follows:

$$A = \int G(E(t)) \cdot E(t) dt$$

where E is a measure of ventilation error, such as absolute ventilation error:

$$E(t) = V_{target} - V_{actual}(t)$$

or relative ventilation error, defined by $$E(t) = \frac{V_{target} - V_{actual}(t)}{V_{target}}$$

It is trivially the case that for some function H $$G(E(t)) \cdot E(t) = H(E(t))$$

The equation above is expressed in terms of G rather than H to indicate that in this integral servocontroller, dA/dt generally increases with E, but that this increase is modified by the factor G(E).

Typically, when E is absolute ventilation error, a gain G of the integral servo-controller of a value in the range 0.1 to 0.3 cmH$_2$O per L/min error in ventilation per second is suitable. However, in servo-controlling the level of ventilation around the target, rapidly and completely meeting the target is not always desirable or necessary. For example, in some short instances of moderate hypoventilation experienced by the patient (i.e., $V_{actual}$ falls below $V_{target}$), it may not be desirable to make a complete and immediate compensation response to the ventilation shortfall. A more rapid or aggressive adjustment might arouse a sleeping patent or otherwise have an unsatisfactory impact on the synchronizabon of the machine with the patient. Such a change may also be less comfortable for the patient. Accordingly, in the preferred embodiment of the invention, the gain G varies depending on the amount by which the measure of ventilation deviates from the target. This permits a slower response to the error when a need for a change in delivered ventilation is detected for minor deviations from the target while also providing a more rapid response to the error for greater deviations from the target. In other words, the gain allows a patient to vary his ventilation around a target ventilation without an aggressive response if he does not stray too far. But if the ventilation does deviate from the target more significantly, a more aggressive response may be taken. Similarly, the gains may be distinct depending on whether the patient's ventilation is above or below the target so that the gain will allow the ventilation support to withdraw more gradually when the patient is over-ventilated since it might not be desirable to rapidly withdraw support that has recently increased as it might cause the patient to oscillate back into being under-ventilated, and the ventilation may appear to be above target because the leak has changed rapidly and the leak compensation system has not substantially compensated for this change.

Figure 4:
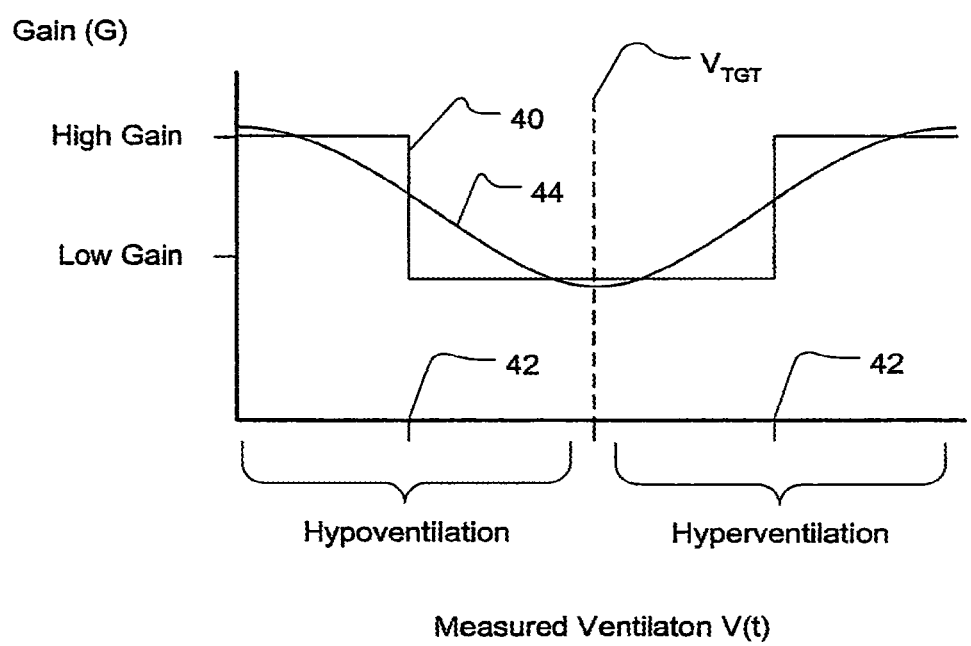
FIG. 4 is a graph of Measured Ventilation V(t) versus Gain G illustrating a symmetrical function for adjusting the servo-ventilator gain that is a function of the distance that the measured ventilation deviates from the target ventilation.

Various methods may be utilized to vary the gain as a function of the distance of the ventilation measure from the ventilation target. In one embodiment as illustrated by symmetrical step function 40 in the graph of FIG. 4, the gain G is a function of a threshold (T) 42. A higher gain per error is implemented for distances greater than the threshold and a lower gain per error for distances below the threshold. For example, the following algorithm can achieve this embodiment:

If d<T then
G=Lower Gain per error
Otherwise
G=Higher Gain per error

Where:
d is the distance from the target $|V_{actual}-V_{target}|$ and
T is a threshold distance.

For example, the typical gain servo of 0.3 cmH$_2$O per L/min per error may be utilized as the higher gain per error and some fraction of higher gain per error would be appropriate for the lower gain per error (e.g., 0.2 cm H$_2$O). In one embodiment, the threshold is a 1.0 liter per minute error where the ventilation measure and target ventilation are minute volumes.

The function 44 is another example in which the gain is varied as a function of the distance of the ventilation measure from the ventilation target. This function is also symmetrical around the target but does not exhibit sharp changes in gain. Moreover, unlike the symmetrical response shown in the previous embodiment, the gain adjustment may also be implemented asymmetrically to permit different gain responses depending on whether the patient's measured ventilation is above or below the ventilation target. These principles are illustrated by the preferred function shown in the graph of FIG. 4A. Those skilled in the art will recognize how to implement the graphed function of relative ventilation error with a ventilator device as illustrated in FIG. 4A.

Figure 4A:
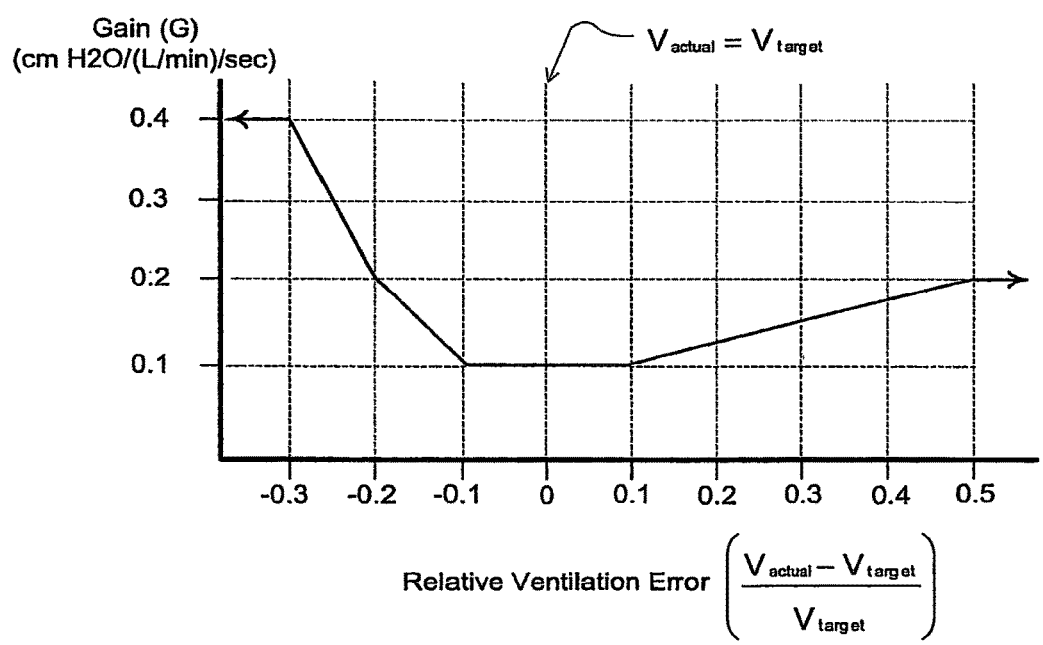
FIG. 4A is a graph of relative ventilation error versus gain illustrating an asymmetrical function for adjusting the servo-ventilator gain that is a function of the distance that the measured ventilation deviates from the target ventilation.

As shown in FIG. 4A, as measured ventilation moves away from the target, the gain may be graduated to increase the ventilation response of the ventilator. However, different gains are applied below and above the target. For respiratory airflows that are above the target value the gains are less than the gains for corresponding respiratory airflows that are below the target value. Thus, for a patient hyperventilating with the relative ventilation error being in excess of 0.5, the gain will not exceed some intermediate gain, e.g., 0.1 cm H$_2$O/(L/min)/sec., since a more aggressive response is not critical. Similarly, since a leak in the system will change the patient's measure of ventilation to make it appear that the patient is hyperventilating, an aggressive response may be incorrect. Conversely, when the patient is hypoventilating to a significant degree (e.g., a relative ventilation error of −0.3), a greater gain is utilized, e.g., 0.3 cm H$_2$O/(L/min)/sec., since a more aggressive response is preferred. In the preferred embodiment, the measure of ventilation is a minute volume or minute ventilation; thus, the gain adjustment is a function of the relative minute ventilation error.

When a gain which varies with error is used, the measure of ventilation used should preferably not change markedly during a breath. Using the measure of ventilation given in the above equation, namely, half the absolute value of respiratory airflow, the change in pressure support during the breath is the integral of the product of the gains and instantaneous errors for a range of ventilations, from a ventilation of zero at the transitions between inspiration and expiration to values of ventilation well above target ventilation at the times of peak inspiratory and expiratory flow (considering a typical breath when ventilation is at target). This works satisfactorily with a constant gain, since gain can then be taken outside the integral, as in the equation above. But with a gain varying with error, such a measure of ventilation which changes substantially during the breath would not allow the desired gain for the ventilation typical of that breath to be delivered; instead the gains for a wide range of ventilations would be traversed, and in particular that for maximum ventilation error would be applied every time the respiratory flow crossed zero. Hence it is necessary to low-pass filter half the absolute value of respiratory flow in order to calculate ventilation and ventilation error before determining the gain. A disadvantage of this low-pass filtering is a delay in the response to changes in ventilation.

One way of using a well-filtered ventilation measure for much of the time but being able to respond to severe hypoventilation quickly is to use two measures of ventilation with different speeds of response. The more rapidly responding measure of ventilation ("fast ventilation"), which fluctuates somewhat during a breath, has no effect on pressure support unless it is moderately below target, from which point as fast ventilation decreases further the more slowly responding measure ("slow ventilation") becomes progressively less important and fast ventilation becomes progressively more important in the calculation of pressure support, until a point is reached below which fast ventilation is the only determiner of pressure support.

In particular, one implementation, using slow and fast relative ventilation errors $E_s$ and $E_f$ respectively, uses the following equation for the rate of change of pressure support amplitude A:

$$\frac{dA}{dt} = \begin{cases} G_s E_x, & \text{when } E_f < 0.3 \\ G_f E_f & \text{when } E_f > 0.5 \\ \alpha G_s E_s + (1-\alpha) G_f E_f & \text{when } 0.3 \leq E_f \leq 0.5, \text{ where} \\ \alpha = \frac{0.5 - E_f}{0.2} \end{cases}$$

Suitable gain values are $G_f=0.7$ and $G_s=0.5$ cm $H_2O$/sec. (The pressure support amplitude A discussed above can be determined by integrating dA/dt.)

C. Alveolar Ventilation Target

Another aspect of the invention involves the control of the ventilator to maintain a ventilation target that more accurately corresponds to actual gas exchange in the patient's respiratory system. This aspect involves servo-control of a measure of alveolar ventilation. While the device as heretofore discussed may utilize a simple minute volume as the target ventilation, in this aspect of the invention the preferred target ventilation $V_{TGT}$ is an alveolar ventilation.

Figure 5:
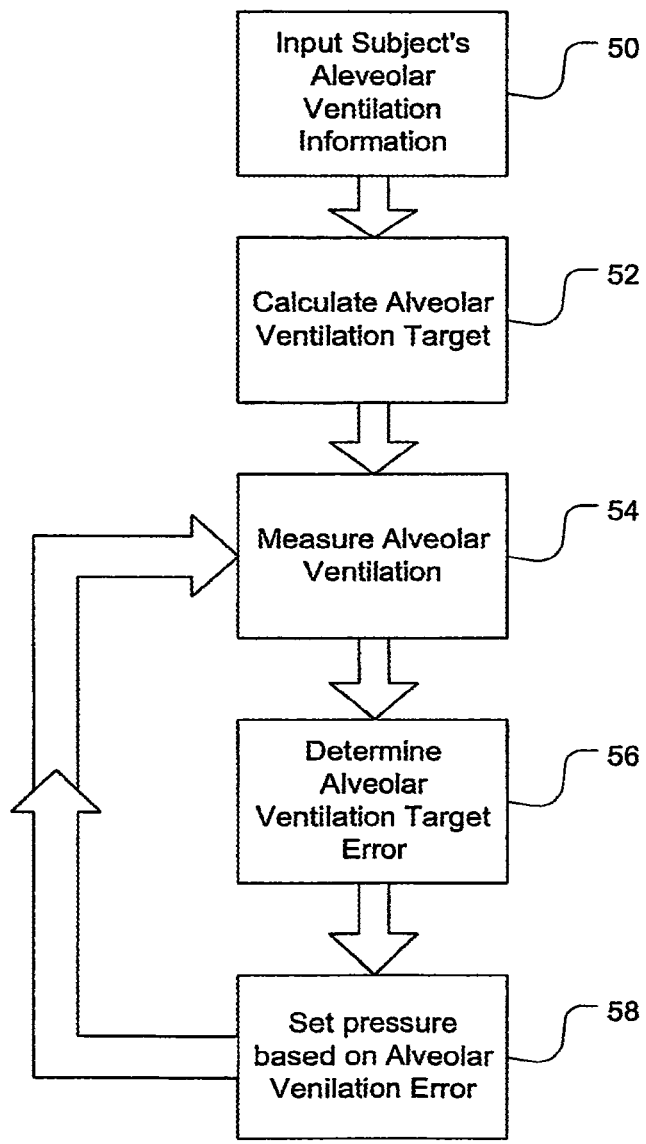
FIG. 5 is a flow chart illustrating steps in the delivery of pressure in accordance with a target alveolar ventilation.

FIG. 5 identifies steps in a methodology of servo-controlling the pressure to maintain alveolar ventilation. In an input step 50, a user is prompted to enter patient specific information necessary to assist with a calculation of an alveolar ventilation target for the patient. In step 52, an alveolar ventilation target is calculated. In step 54, a measure of alveolar ventilation is taken. In step 56, the measure and target are compared to derive an alveolar ventilation target error. In step 58, the pressure is adjusted based on the alveolar ventilation target error.

In order for the device to control such a ventilation measure, an estimate of the patient's physiologic dead space $V_D$ (i.e., alveolar plus anatomical dead space) is required. In a simple embodiment, prior to the control of alveolar ventilation, as previously mentioned the user may be prompted to enter an estimate into the device in step 50. Thus, the user may enter alveolar volume $V_A$ or dead space volume $V_D$ determined from a prior analysis of the patient. $V_D$ may be determined by any known method for analyzing dead space such as by using Fowler's method or Bohr's method. The Fowler and Bohr methods for determining dead space volume are described by John B. West in *Respiratory Physiology*—the essentials 5th ed., Baltimore Md., Williams & Wilkins, 1995. Alternatively, $V_D$ may be a fixed volume or it may be a default volume if no other information is entered or calculated, for example, 150 ml.

Alternatively, the device may estimate anatomical dead space volume from a table based on user responses to questions regarding the size of the patient. For example, prior to use, the device may prompt a user for height, age and sex. With this information, the device may access a table or tables with such information associated with ideal weights for such a user. With the determined ideal weight of such a patient, anatomical dead space may be estimated by allowing 2 ml of anatomical dead space volume for each 1 kg of ideal weight. As those skilled in the art will recognize, the table may contain the anatomical dead space based on age, height and sex rather than the weight based on the one-to-one approximation noted above. The ideal weights for patients based on age, height and sex are known in the art. In one embodiment, the device may prompt the user for the actual weight and anatomical dead space volume or it may be approximated therefrom based on the above formula. This weight may also be adjusted based on the patient's body mass, such as by entry of a body mass index (BMI) or a skin fold thickness. Those skilled in the art will recognize various ways for utilizing a table or other formula or calculation to approximate anatomical dead space volume from the size of the patient. In one embodiment, the above weight-related estimate of anatomical dead space may be taken as $V_D$ or the estimate for both the alveolar and anatomic dead space. Alternatively, a separate estimate for alveolar dead space may be made and combined with the anatomical dead space. Thus, additional prompting of the device may also provide an estimate of alveolar dead space $V_{ALD}$ that will be combined with the anatomical dead space $V_{AND}$ to serve as the estimate of total dead space volume $V_D$ (i.e., the physiological dead space $[V_D = V_{ALD} + V_{AND}]$).

Figure 6:
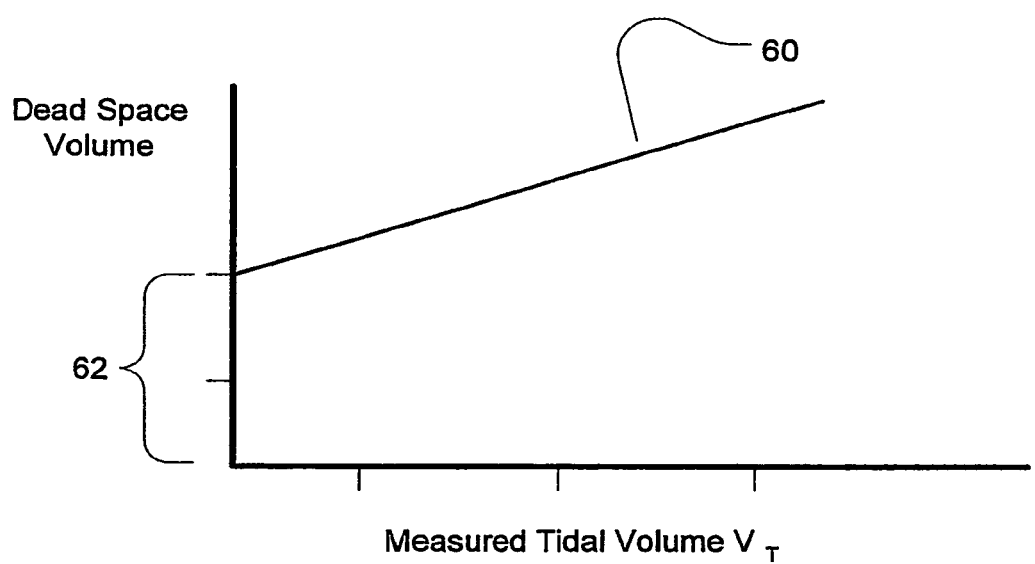
FIG. 6 is a graph of a function for determining dead space as a function of tidal volume.

In one embodiment of the invention, the dead space $V_D$ may be taken to be a function of the patient's expected tidal volume or a recently calculated tidal volume measured during the provision of treatment as follows: $V_D = F(V_T)$. In such an embodiment, the function may be a fixed percent in a range of about 0.2 to 0.35 or roughly about 30% or about ⅓ of the tidal volume for normal patients at rest and higher for patients with a lung disease such as Chronic Obstructive Pulmonary Disease at rest. Given that certain patients with lung disease will have a greater degree of dead space than normal patients, in one embodiment the device may prompt input from a user to determine if the patient has a lung disease or COPD (for example, Emphysema or Chronic Bronchitis). The fixed percent may be set to a value at the higher end of the range for such patients, otherwise it will be set to the lower end of the range if the response is in the negative. Alternatively, an affine function based on tidal volume may be utilized to derive $V_D$ and, optionally this affine function may also depend on the disease condition of the patient as prompted by the device. For example, as illustrated in FIG. 6, an affine function 60 may be utilized as a function of tidal volume to determine dead space. Optionally, different functions may be selected depending on whether the patient suffers from COPD, or any such particular disease. Thus a specified volume offset 62 associated with the patient's disease or the alveolar dead space ($V_{ALD}$)) may be applied to the patient's function of tidal volume as illustrated in FIG. 6. In still another embodiment of the invention, the $V_D$ may be estimated with use of an electronically integrated monitor to measure arterial partial pressure carbon dioxide $PCO_2$ or alternatively expired $CO_2$ in the mask. The $CO_2$ data may be utilized to derive an alveolar ventilation target during a learning period in accordance with Bohr's equation and then used for servo-controlling support to equal the target alveolar ventilation.

As previously noted, the preferred target $V_{target}$ is an alveolar minute volume. During the calculation step 52 of FIG. 5, the device may be configured or programmed with the following formula to calculate alveolar minute volume target.

$$\text{Alveolar minute volume } (V_{alveolar\text{-}minute}) = V_A \times R$$

where $V_A$ is the alveolar volume ($V_A = V_T - V_D$)

$V_T$ is the patient's expected tidal volume $V_D$ is the patient's dead space volume, and R is the patient's expected respiratory rate (breaths/min). Alternatively, the target may be set as a function of this calculated $V_{alveolar\text{-}minute}$. For example, the target may be set to 95% of this calculated $V_{alveolar\text{-}minute}$.

For purposes of the expected values utilized in this determination, in step 50 the device may also prompt for the entry of the patient's expected tidal volume $V_T$ and expected respiratory rate R. However, such patient specific information may be measured by the device during an awake learning period or calculated based upon the entry of some of the above-identified information. For example, the respiratory rate may be taken as a median respiratory rate over the last 75% of an awake learning period. Optionally, where the target calculation is based on measures taken from an awake learning period, such as the respiratory rate, the calculation of the target alveolar minute volume may be adjusted to account for respiratory differences associated with sleep as described in commonly owned U.S. Pat. No. 6,644,312, the disclosure of which is incorporated herein by reference.

A mean alveolar ventilation during part of a learning period can be calculated as follows. For each breath, there is a tidal volume $V_T$, and if there are N breaths over a time T and the alveolar tidal volume is given as a function of tidal volume by the function a $(V_T)$, then the mean alveolar ventilation is given by $$\frac{1}{T}\sum_{i=1}^{N} a(V_{T,i})$$

But when a median alveolar ventilation is required, which is desirable in order to reject outliers and artifacts, a breathwise median is inappropriate since it gives the same weight to short breaths (typically lower in tidal volume) as to longer breaths, and so typically does not give the same result as mean ventilation in cases where it should, such as a distribution of alveolar ventilation with respect to time which is symmetrical with respect to the mean. This is undesirable. A timewise median is more desirable. Mathematically, a piecewise constant function of time is constructed by assigning to the time period of each breath the alveolar ventilation (alveolar volume divided by breath duration) during that breath, and calculating the median of this function. In practice, an approximation to this can be efficiently calculated by forming a histogram of alveolar ventilation. For each breath, the alveolar ventilation is calculated, and the corresponding entry in the histogram is incremented by an amount proportional to the duration of the breath. The median of the histogram is then calculated in the usual way.

The measurement of the actual delivered alveolar ventilation $V_{actual}$ experienced by the patient in step 54 is based on the same formula as the target calculation with the exception that the tidal volume $V_T$ and the respiratory rate are recent measures preferably determined continuously from the measure of respiratory airflow from the patient. For example, the respiratory rate is the recent average respiratory rate or the number of breaths taken by the patient over the previous one-minute period. The tidal volume is the volume from the previous breath or average volume from the breaths taken during the previous one-minute period. Tidal volume may also be determined by dividing a measure of minute ventilation by respiratory frequency ($V_{min}/f_{resp}$). Preferably, minute ventilation can be derived by filtering half the absolute value of respiratory airflow with a fourth-order low pass Bessel filter with a time constant selected to achieve the minute average. The patient's dead space volume $V_D$ as entered may remain constant or vary as a function of tidal volume as described above.

Alternatively, the actual delivered alveolar ventilation $V_{alveolar}$ (or the target based on expected values) may be calculated according to the formula:

$$V_{alveolar} = \left(\frac{V_{total}}{f_{resp}} - V_D\right) f_{resp}$$

where:

$V_{total}$ is a ventilation derived from airflow such as half the absolute value of respiratory airflow, low pass filtered with a corner frequency chosen to give a response appropriate for the application (for control, significantly faster than the servocontrolling response, to avoid oscillations; for target determination, possibly quite slow), $V_D$ is the dead space volume determined from any one of the methods previously described, and $f_{resp}$ is the respiratory frequency (breaths per minute) which may be calculated as the number of revolutions per minute of the instantaneous phase variable as described previously.

The preferred method of calculating alveolar ventilation is as follows:

Suppose that the alveolar volume delivered as a function of volume V inhaled above FRC (functional residual capacity, the lung volume at the end of expiration) is given by U(V). Then, both during inspiration and expiration, the following value is input to a lowpass filter whose output is the measure of alveolar ventilation:

$$\frac{1}{2}|Q|U'\left(\int_{t_0}^{t}|Q|ds\right)$$

where Q is respiratory flow as a function of time, the prime symbol indicates the derivative, and $t_0$ is the time of the start of the most recent inspiration or expiration.

Intuitively, the half the absolute value of respiratory flow is multiplied by the rate at which the alveolar volume is increasing, relative to volume. For the special case of excluding only the anatomical deadspace $V_{DA}$ from the calculated alveolar ventilation, this is equivalent to calculating the volume since the beginning of the most recent inspiration or expiration, and when this volume is less than the deadspace, making the input to the lowpass filter zero, and otherwise making the input equal to half the absolute value of respiratory flow. This is because here we have $$U(V)\begin{cases} 0, & \text{when } 0 \le V \le V_{DA} \\ V - V_{DA}, & \text{otherwise} \end{cases}$$

so that $$U'(V) = \begin{cases} 0, & \text{when } 0 \le V \le V_{DA} \\ 1, & \text{otherwise} \end{cases}$$

The advantages of using both inspiratory and expiratory flow in the calculation of ventilation, rather than either inspiratory or expiratory flow alone, include lower sensitivity to baseline error in flow, and a smoother filter output.

Once the actual and target alveolar ventilations are determined, delivered pressure support amplitude A can be adjusted based upon the error, for example, as follows:

$$A = -G\int(V_{alveolar-minute}(t) - V_{target})dt$$

The delivered pressure is then set in accordance with the amplitude A as previously discussed.

D. Decreasing Pressure Support Adjustment When Leak is Changing Rapidly.

Rapid change in leak causes the respiratory flow baseline to be transiently incorrect, which almost always has the effect of making calculated ventilation higher than actual ventilation, with the result that pressure support is either inappropriately reduced, or increased more slowly than it should be.

U.S. Pat. No. 6,532,957 mentioned above, by Berthon-Jones, describes one method of decreasing this effect, using a fuzzy quantity called "jamming".

In the present invention, to decrease this effect, a different fuzzy measure R, where 0≤R≤1, of the extent to which leak is changing rapidly, is used to decrease the rate of pressure support adjustment, by multiplying the rate of adjustment of pressure support amplitude dA/dt, as calculated above, by 1−R. To calculate R, the estimated respiratory flow is processed with a lowpass filter having a peak hold tendency, producing an estimate L of residual leak (defined to be leak which is not compensated for) which typically responds more rapidly that the leak estimate does, and so warns that the leak estimate is incorrect, though by itself fluctuating too rapidly to be directly useful as a leak estimate for the purposes of calculation of respiratory flow. When the absolute value of L is small (for example, less than the target ventilation), R is 0; when the absolute value of L is large (for example, twice the target ventilation), R is 1; and in between, it is interpolated linearly.

An implementation of the filter which produces L is as follows. The first stage is a 4-pole Bessel lowpass filter with a corner frequency of 3.2/60 Hz. The second stage is an instant-rise, variable time constant first order lowpass fall filter, where "rise" here means an increase in the direction of the previous output away from zero; so, for example, if the previous value of the output was negative, a "rise" means becoming more negative. A "fall" means movement towards zero. The time constant is longer when the flow is further from zero. Let the filtered respiratory flow (output of the first stage) relative to the target ventilation (both in the same flow units) be given by $$Q_R = \frac{Q_{respiratory, filtered}}{V_{target}}$$

Then the fall rate constant (reciprocal of the fall time constant) in units of 1/sec is given by 1/0.5 when $Q_R \leq 0.75$ 1/5 when $Q_R \geq 2$ $\alpha/5 + (1-\alpha)/0.5$ otherwise, where $$\alpha = \frac{Q_R - 0.75}{1.25}$$

The purpose of the second stage is to cause the output of the second stage to be held closer to those values of the output of the first stage which are further away from zero. (The output of the first stage typically has the appearance of a sinusoid plus a slowly changing "DC" value.)

This method of compensating for residual leak has the advantage over the "jamming" described in Berthon-Jones U.S. Pat. No. 6,532,957 in that it is able to detect residual leak which is not large enough to produce apparent inspiratory or expiratory periods much longer than normal (to produce these long periods generally requires a baseline shift large enough to make estimated respiratory flow positive throughout or during most of expiration, for example, in the case where leak has suddenly increased).

Although the invention has been described with reference to various embodiments as described in this entire disclosure, it is to be understood that these embodiments are merely illustrative of an application of the various principles of the invention. Numerous modifications, in addition to the illustrative embodiments of the invention discussed herein, may be made and other arrangements may be devised without departing from the spirit and scope of the invention.

The invention claimed is:

1. A method for adjusting the-ventilatory pressure support provided to a patient comprising:
   determining, with a processor, a flow rate of air delivered to the patient and calculating therefrom a measure of a function of respiratory airflow of the patient,
   determining, with the processor, an adjustment to the ventilatory pressure support in a direction that tends to reduce a difference between the measure of the function of respiratory airflow and a target value, and
   determining, with the processor, a rate at which the determined adjustment of ventilatory pressure support is made based on a magnitude of the difference between the measure of the function of respiratory airflow and the target value such that the rate is a product of a gain and a ventilation error, the ventilation error comprising the magnitude of the difference, and wherein said gain is also varied as a function of the ventilation error; and
   controlling, with the processor, the adjustment of ventilatory pressure support, wherein an increase of the magnitude of the difference between the measure of the function of respiratory airflow and the target value corresponds to an increase in the rate at which the determined adjustment is made.

2. A method of adjusting the ventilatory pressure support provided to a patient in accordance with claim 1, wherein the measure of a function of respiratory airflow of the patient is a measure of patient ventilation, and the target value is a target ventilation.

3. A method of adjusting the ventilatory pressure support provided to a patient in accordance with claim 2, wherein the adjustment of ventilatory pressure support when the patient ventilation is below the target ventilation is controlled at a rate that is greater than the rate at which the ventilatory pressure support is adjusted when the patient ventilation is above the target.

4. A method of adjusting the ventilatory pressure support provided to a patient in accordance with claim 2, wherein the target ventilation is predetermined.

5. A method of adjusting the ventilatory pressure support provided to a patient in accordance with claim 4, wherein the target ventilation is a percentage of the patient's recent average ventilation.

6. A method of adjusting the ventilatory pressure support provided to a patient in accordance with claim 2, wherein the ventilatory pressure support is synchronized to the patient's breathing by flow triggering and phase cycling.

7. A method of adjusting the ventilatory pressure support provided to a patient in accordance with claim 1, wherein the measure of a function of respiratory airflow of the patient is a measure of alveolar patient ventilation, and the target value is an alveolar target ventilation, wherein both the alveolar target ventilation and the alveolar patient ventilation take into account the patient's physiologic dead space.

8. A method of adjusting the ventilatory pressure support provided to a patient in accordance with claim 7 wherein the patient's physiologic dead space that is taken into account includes both alveolar and anatomical dead space.

9. A method of adjusting the ventilatory pressure support provided to a patient in accordance with claim 7 wherein the patient's physiologic dead space that is taken into account is determined based on a size, weight or body mass index of the patient.

10. A method of adjusting the ventilatory pressure support provided to a patient in accordance with claim 7 wherein the patient's physiologic dead space that is taken into account is determined based on a tidal volume measurement taken for the patient.

11. A method of adjusting the ventilatory pressure support provided to a patient in accordance with claim 1, wherein the adjustment of ventilatory pressure support is controlled to allow ventilation support to be withdrawn more gradually when the patient is over-ventilated than when the patient is under-ventilated.

12. A method of adjusting the ventilatory pressure support provided to a patient in accordance with claim 1 further comprising:
   calculating, with the processor, either an absolute or relative difference between the measure of the function of respiratory airflow of the patient and the target value;
   deriving, with the processor a pressure support amplitude that is a function of a product of the calculated difference and a gain that increases with the calculated difference; and
   controlling, with the processor, a delivery of air to the patient at a pressure that is a function of said pressure support amplitude.

13. A method of adjusting the ventilatory pressure support provided to a patient in accordance with claim 12 wherein said pressure support amplitude changes at a rate that is a function of both magnitude and sign of the calculated difference.

14. A method of adjusting the ventilatory pressure support provided to a patient in accordance with claim 12 wherein said pressure support amplitude changes at a rate that is controlled to be faster for measures of the function of respiratory airflow of the patient below said target value than for measures of the function of respiratory airflow of the patient above said target value.

15. A method of adjusting the ventilatory pressure support provided to a patient in accordance with claim 1 further comprising:
   determining, with the processor, a phase of the patient's breathing cycle; and
   controlling, with the processor, a blower to deliver air to the patient at a pressure that is a function of an amplitude that is appropriate for a normal breathing cycle at the determined phase.

16. A method of adjusting the ventilatory pressure support provided to a patient in accordance with claim 15 further comprising determining, with the processor, the phase of the patient's breathing cycle by relating respiratory airflow and its rate of change to different phases of a normal breathing cycle.

17. A method of adjusting the ventilatory pressure support provided to a patient in accordance with claim 16, further comprising applying, with the processor, a set of fuzzy logic rules.

18. A method of adjusting the ventilatory pressure support provided to a patient in accordance with claim 15 wherein said amplitude is the amplitude at the determined phase of the patient's breathing cycle of an amplitude-versus-phase template that is appropriate for a normal breathing cycle.

19. The method of claim 1 wherein by the variation of said gain, the gain has one of a first or a second value depending on whether the difference between the measure of the function of respiratory airflow and the target value is greater than or less than a threshold value.

20. Apparatus for providing ventilatory assistance to a spontaneously breathing patient comprising:
   a processor for determining a flow rate of air delivered to the patient, computing a measure of a difference between a function of respiratory airflow and a target value, determining an adjustment to ventilation support in a direction that tends to reduce a difference between the measure of the function of respiratory airflow and a target value, and determining a rate at which the determined adjustment of ventilation support is made based on a magnitude of the difference between the measure of the function of respiratory airflow and the target value, and
   a controller for controlling a blower to deliver breathable gas to the patient at a pressure that is a function of said difference measure, the controller using a blower in a servo-controlled loop with a gain that varies depending on a magnitude of said difference measure such that the rate is a product of the gain and a ventilation error, the ventilation error comprising the magnitude of the difference, and wherein said gain is also varied as a function of the ventilation error.

21. Apparatus for providing ventilatory assistance in accordance with claim 20 wherein for respiratory airflows that are above said target value the controller uses gains that are less than the gains for corresponding respiratory airflows that are below said target value.

22. Apparatus for providing ventilatory assistance in accordance with claim 20 wherein said difference measure is a clipped integral of the respiratory airflow minus said target value, and for either polarity of said difference measure said controller causes the pressure of the delivered breathable gas to be changed in a respective direction that tends to reduce said difference measure.

23. Apparatus providing ventilatory assistance in accordance with claim 20 wherein the difference measure is a measure of the difference between said function of respiratory airflow and said target value over a period of time.

24. Apparatus for providing ventilatory assistance in accordance with claim 20 wherein said target value is an alveolar ventilation that takes into account the patient's physiologic dead space.

25. Apparatus for providing ventilatory assistance in accordance with claim 20 wherein the blower allows ventilation support to be withdrawn more gradually when the patient is over-ventilated than when the patient is under-ventilated.

26. Apparatus for providing ventilatory assistance in accordance with claim 20 wherein the computing of the difference measure comprises determining the patient's ventilation and calculating therefrom either an absolute or relative ventilation error compared to the target value, said controller deriving a pressure support amplitude that is a function of a product of the ventilation error and a gain that increases with ventilation error; said apparatus further comprising a blower for delivering the breathable gas to the patient at a pressure that is a function of said pressure support amplitude.

27. Apparatus for providing ventilatory assistance in accordance with claim 26 wherein said pressure support amplitude changes at a rate that is a function of both a magnitude and sign of the ventilation error.

28. Apparatus for providing ventilatory assistance in accordance with claim 26 wherein said pressure support amplitude changes at a rate that is controlled to be faster for ventilation errors below said target value than for ventilation errors above said target value.

29. Apparatus for providing ventilatory assistance in accordance with claim 20 wherein the processor is further for determining a phase of the patient's breathing cycle, and wherein the controller is further for controlling the blower to deliver the breathable gas to the patient at a pressure that is a function of an amplitude that is appropriate for a normal breathing cycle at the determined phase.

30. Apparatus for providing ventilatory assistance in accordance with claim 29 wherein said processor is further for determining the phase of the patient's breathing cycle by relating respiratory airflow and its rate of change to different phases of a normal breathing cycle.

31. Apparatus for providing ventilatory assistance in accordance with claim 30, wherein said processor further applies a set of fuzzy logic rules.

32. Apparatus for providing ventilatory assistance in accordance with claim 29 wherein said amplitude is the amplitude at the determined phase of a current breathing cycle of an amplitude-versus-phase template that is appropriate for a normal breathing cycle.

33. Apparatus for providing ventilatory assistance in accordance with claim 29, wherein said gain is non-decreasing as the absolute value of said difference measure increases.

34. Apparatus for providing ventilatory assistance in accordance with claim 20 wherein the function of respiratory airflow is a measure of patient ventilation, and wherein the target value is a target ventilation.

35. Apparatus for providing ventilatory assistance in accordance with claim 34, wherein the controller uses asymmetrical gains for corresponding values of the measure of patient ventilation that are below or above said target ventilation.

36. Apparatus for providing ventilatory assistance in accordance with claim 20, wherein the breathable gas is air.

37. The apparatus of claim 20 wherein by the variation of said gain, the gain has one of a first or a second value depending on whether the difference between the measure of the function of respiratory airflow and the target value is greater than or less than a threshold value.

* * * * *